(12) United States Patent
Pederson, Jr. et al.

(10) Patent No.: US 11,110,248 B2
(45) Date of Patent: Sep. 7, 2021

(54) MEDICAL DEVICE RELEASE SYSTEM

(71) Applicant: BOSTON SCIENTIFIC SCIMED, INC., Maple Grove, MN (US)

(72) Inventors: Gary J. Pederson, Jr., Albertville, MN (US); Mary-Claire Anderson, Minneapolis, MN (US); Ken Xiao Kang Zhang, Maple Grove, MN (US); David D. Groneberg, Plymouth, MN (US); Nicholas L. Tassoni, Andover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 64 days.

(21) Appl. No.: 15/813,852

(22) Filed: Nov. 15, 2017

(65) Prior Publication Data

US 2018/0133435 A1  May 17, 2018

Related U.S. Application Data

(60) Provisional application No. 62/423,466, filed on Nov. 17, 2016.

(51) Int. Cl.
*A61M 25/00* (2006.01)
*A61B 17/12* (2006.01)
(Continued)

(52) U.S. Cl.
CPC ..... *A61M 25/0021* (2013.01); *A61B 17/1214* (2013.01); *A61B 17/12145* (2013.01);
(Continued)

(58) Field of Classification Search
CPC .......... A61B 17/12145; A61B 17/1214; A61B 2017/12054; A61B 2090/037;
(Continued)

(56) References Cited

U.S. PATENT DOCUMENTS 3,342,179 A * 9/1967 Ellmann ................ A61M 1/02
604/408
5,117,839 A  6/1992 Dance
(Continued)

FOREIGN PATENT DOCUMENTS

JP           10192290 A       7/1998
WO        2007070797 A2      6/2007
WO     WO 2007070797    *   6/2007

OTHER PUBLICATIONS

PCT Application No. PCT/US2017/061779 International Search Report and Written Opinion, dated Feb. 26, 2018.

*Primary Examiner* — Theodore J Stigell
(74) *Attorney, Agent, or Firm* — Seager, Tufte & Wickhem LLP

(57) ABSTRACT

A medical device system may include an elongate shaft having a lumen extending from a proximal end of the elongate shaft to a distal end of the elongate shaft, a medical device disposed proximate the distal end of the elongate shaft, a release wire disposed within the lumen of the elongate shaft, wherein the release wire releasably secures the medical device to the distal end of the elongate shaft, a securement member fixedly attached to the proximal end of the elongate shaft and to a proximal end of the release wire, and a microcatheter configured to deliver the medical device to a treatment site, the elongate shaft and the medical device being slidably disposed within a lumen of the microcatheter. A proximal portion of the securement member may be configured to disengage from a distal portion of the securement member.

14 Claims, 10 Drawing Sheets

(51) Int. Cl.
  *A61M 25/01* (2006.01)
  *A61B 17/00* (2006.01)
  *A61B 90/00* (2016.01)

(52) U.S. Cl.
  CPC . *A61M 25/0147* (2013.01); *A61B 2017/0046* (2013.01); *A61B 2017/00477* (2013.01); *A61B 2017/00867* (2013.01); *A61B 2017/12054* (2013.01); *A61B 2090/037* (2016.02); *A61M 25/0108* (2013.01); *A61M 25/0127* (2013.01); *A61M 2025/0042* (2013.01); *A61M 2205/0216* (2013.01)

(58) Field of Classification Search
  CPC ...... A61B 2017/0046; A61M 25/0021; A61M 25/0108; A61M 25/0127; A61M 2025/0042; A61M 25/0147; A61M 2205/0216
  USPC ........................................................ 604/160
  See application file for complete search history.

(56) References Cited

U.S. PATENT DOCUMENTS

| | | |
|---|---|---|
| 5,250,071 A | 10/1993 | Palermo |
| 5,282,478 A | 2/1994 | Fleischhaker, Jr. et al. |
| 5,304,195 A | 4/1994 | Twyford, Jr. et al. |
| 5,546,958 A | 8/1996 | Thorud et al. |
| RE37,117 E | 3/2001 | Palermo |
| 6,491,646 B1 | 12/2002 | Blackledge |
| 2007/0282373 A1 | 12/2007 | Ashby et al. |
| 2008/0109059 A1 | 5/2008 | Gordon et al. |
| 2008/0119891 A1 | 5/2008 | Miles et al. |
| 2008/0269719 A1 | 10/2008 | Balgobin et al. |
| 2008/0300616 A1 | 12/2008 | Que et al. |
| 2009/0043331 A1 | 2/2009 | Buiser et al. |
| 2012/0046687 A1 | 2/2012 | Trommeter et al. |
| 2015/0335333 A1 | 11/2015 | Jones et al. |
| 2016/0228123 A1 | 8/2016 | Anderson et al. |
| 2020/0229957 A1* | 7/2020 | Bardsley .......... A61B 17/12113 |

* cited by examiner

MEDICAL DEVICE RELEASE SYSTEM

CROSS-REFERENCE TO RELATED APPLICATIONS

This application claims priority under 35 U.S.C. § 119 to U.S. Provisional Application Ser. No. 62/423,446, filed Nov. 17, 2016, the entirety of which is incorporated herein by reference.

TECHNICAL FIELD

The present disclosure pertains to medical devices and methods for manufacturing and/or using medical devices. More particularly, the present disclosure pertains to configurations of a system for releasing for medical implants.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a medical device system may comprise an elongate shaft having a lumen extending from a proximal end of the elongate shaft to a distal end of the elongate shaft, a release wire disposed within the lumen of the elongate shaft, wherein the release wire is configured to releasably attach a medical device to the distal end of the elongate shaft, and a securement member fixedly attached to the proximal end of the elongate shaft and to a proximal end of the release wire. A proximal portion of the securement member may be configured to disengage from a distal portion of the securement member.

In addition or alternatively, and in a second aspect, the proximal portion of the securement member is fixedly attached to the proximal end of the release wire and the distal portion of the securement member is fixedly attached to the proximal end of the elongate shaft.

In addition or alternatively, and in a third aspect, an outer surface of the distal portion of the securement member is fixedly attached to an inner surface of the elongate shaft.

In addition or alternatively, and in a fourth aspect, disengaging the proximal portion of the securement member from the distal portion of the securement member permits the release wire to axially translate relative to the elongate shaft.

In addition or alternatively, and in a fifth aspect, axial translation of the proximal portion of the securement member relative to the distal portion of the securement member axially translates the release wire relative to the elongate shaft.

In addition or alternatively, and in a sixth aspect, the proximal portion of the securement member is integrally formed with the distal portion of the securement member.

In addition or alternatively, and in a seventh aspect, the securement member includes a perforation formed in a wall of the securement member.

In addition or alternatively, and in an eighth aspect, the proximal portion of the securement member is disposed proximal of the perforation and the distal portion of the securement member is disposed distal of the perforation.

In addition or alternatively, and in a ninth aspect, the securement member includes a frangible link formed in a wall of the securement member.

In addition or alternatively, and in a tenth aspect, the proximal portion of the securement member is disposed proximal of the frangible link and the distal portion of the securement member is disposed distal of the frangible link.

In addition or alternatively, and in an eleventh aspect, a medical device system may comprise an elongate shaft having a lumen extending from a proximal end of the elongate shaft to a distal end of the elongate shaft, a medical device disposed proximate the distal end of the elongate shaft, a release wire disposed within the lumen of the elongate shaft, wherein the release wire releasably secures the medical device to the distal end of the elongate shaft, a securement member fixedly attached to the proximal end of the elongate shaft and to a proximal end of the release wire, and a microcatheter configured to deliver the medical device to a treatment site, the elongate shaft and the medical device being slidably disposed within a lumen of the microcatheter. A proximal portion of the securement member may be configured to disengage from a distal portion of the securement member.

In addition or alternatively, and in a twelfth aspect, the proximal portion of the securement member is configured to disengage from the distal portion of the securement member at a location proximal of the microcatheter when the medical device is disposed distal of the microcatheter.

In addition or alternatively, and in a thirteenth aspect, the proximal portion of the securement member is configured to disengage from the distal portion of the securement member at a perforation formed in a wall of the securement member.

In addition or alternatively, and in a fourteenth aspect, the elongate shaft includes a first portion of a release mechanism attached to the distal end of the elongate shaft and the medical device includes a second portion of the release mechanism attached to a proximal end of the medical device. The release wire may interlock the first portion of the release mechanism with the second portion of the release mechanism when the proximal portion of the securement member is engaged with the distal portion of the securement member.

In addition or alternatively, and in a fifteenth aspect, the proximal portion of the securement member is disengaged from the distal portion of the securement member by bending, twisting, or pulling the proximal portion of the securement member relative to the distal portion of the securement member.

In addition or alternatively, and in a sixteenth aspect, a method of delivering a medical device to a treatment site may comprise: inserting a microcatheter into a patient's anatomy and guiding a distal end of the microcatheter to a location adjacent the treatment site; inserting a medical device disposed at a distal end of an elongate shaft into a proximal end of a lumen disposed within the microcatheter; wherein the medical device is releasably attached to the distal end of the elongate shaft by a pull wire extending through a lumen within the elongate shaft, and wherein a securement member extends proximally from the elongate shaft, the securement member being fixedly attached to the elongate shaft and the pull wire; advancing the medical device through the microcatheter to the treatment site; disengaging a proximal portion of the securement member from a distal portion of the securement member; and translating the pull wire relative to the elongate shaft, thereby releasing the medical device from the elongate shaft.

In addition or alternatively, and in a seventeenth aspect, disengaging the proximal portion of the securement member from the distal portion of the securement member includes moving the proximal portion of the securement member relative to the distal portion of the securement member to separate the proximal portion of the securement member from the distal portion of the securement member.

In addition or alternatively, and in an eighteenth aspect, the proximal portion of the securement member is fixedly attached to the pull wire and the distal portion of the securement member is fixedly attached to the elongate shaft.

In addition or alternatively, and in a nineteenth aspect, a first portion of a release mechanism is attached to the distal end of the elongate shaft and a second portion of the release mechanism is attached to a proximal end of the medical device.

In addition or alternatively, and in a twentieth aspect, the pull wire is slidably disposed within the distal portion of the securement member, the elongate shaft, the first portion of the release mechanism, and the second portion of the release mechanism.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
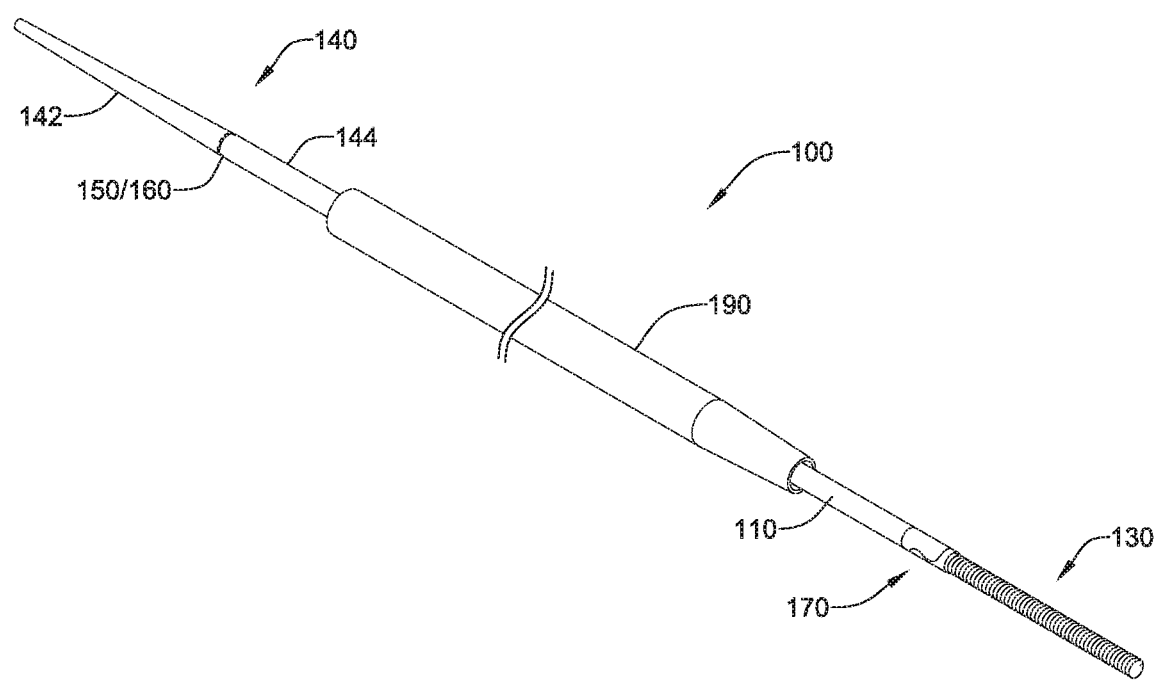
FIG. 1 is a perspective view of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Figure 2:
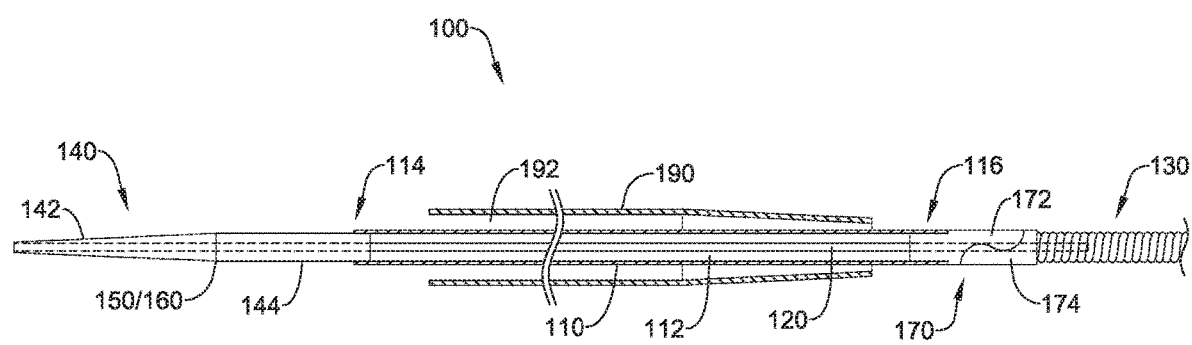
FIG. 2 is a partial cut-away view of an example medical device system.

FIGS. 1 and 2 illustrate aspects of an example medical device system 100. The medical device system 100 may include an elongate shaft 110 having a lumen 112 extending from a proximal end 114 of the elongate shaft 110 to a distal end 116 of the elongate shaft 110. In some embodiments, the elongate shaft 110 may be a catheter, a hypotube, or other similar tubular structure. Some suitable but non-limiting materials for the elongate shaft 110, for example metallic materials, polymer materials, composite materials, etc., are described below.

The medical device system 100 may include a release wire 120 slidably disposed within the lumen 112 of the elongate shaft 110. A medical device 130 may be disposed proximate the distal end 116 of the elongate shaft 110. The release wire 120 may be configured to releasably attach the medical device 130 to the distal end 116 of the elongate shaft 110. For simplicity, the medical device 130 is illustrated herein as a shape memory embolic coil, such as those used to treat aneurysms for example, but other suitable medical devices transported, delivered, used, released etc. in a similar manner are also contemplated, including but not limited to stents, embolic filters, replacement heart valves, occlusion devices, and/or other medical implants, etc. In some embodiments, the release wire 120 may be alternately and/or interchangeably referred to as a pull wire, an actuation wire, and/or a locking wire. The release wire 120 may generally be a solid wire or shaft, but may also be tubular in some embodiments. Some suitable but non-limiting materials for the release wire 120, for example metallic materials, polymer materials, composite materials, etc., are described below.

In some embodiments, the medical device system 100 may include a microcatheter 190 sized and configured to deliver the medical device 130 to a treatment site. The elongate shaft 110 and the medical device 130 may be slidably disposed within a lumen 192 of the microcatheter 190. In some embodiments, the microcatheter 190 may facilitate percutaneous delivery of the medical device 130 to the treatment site. Some suitable but non-limiting materials for the microcatheter 190, for example metallic materials, polymer materials, composite materials, etc., are described below.

Figure 3:
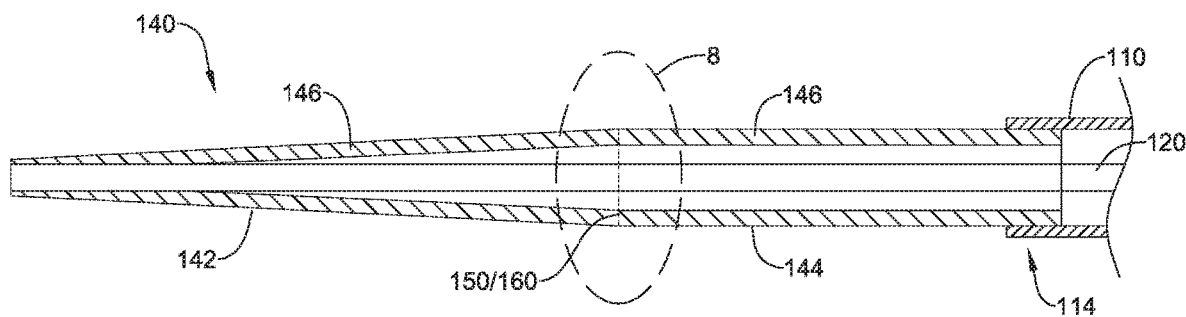
FIG. 3 is partial cut-away view of a portion of an example medical device system.
Figure 4:
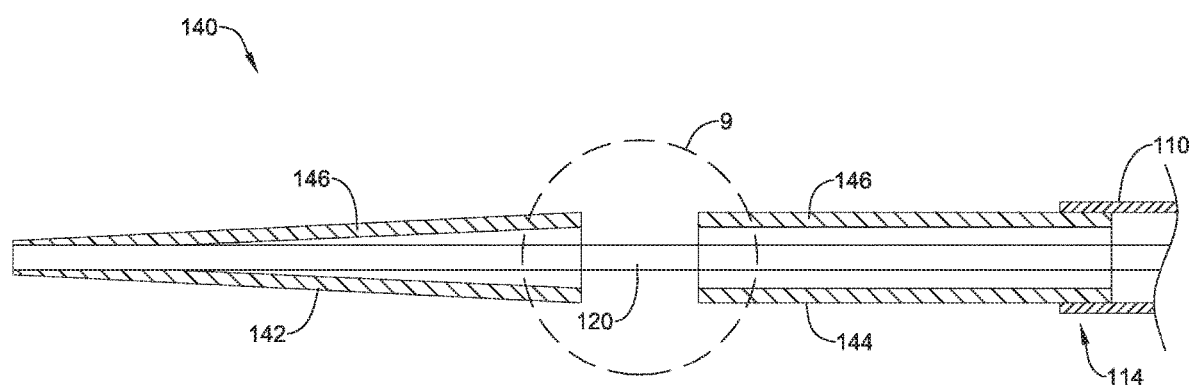
FIG. 4 is partial cut-away view of a portion of an example medical device system.

The medical device system 100 may include a securement member 140 fixedly attached to and/or extending proximally from the proximal end 114 of the elongate shaft 100, and fixedly attached to a proximal end of the release wire 120. The securement member 140 may include a proximal portion 142, a distal portion 144, and a wall 146 (as seen in FIGS. 3 and 4, for example) extending from a proximal end of the securement member 140 to a distal end of the securement member 140. In at least some embodiments, the proximal portion 142 of the securement member 140 may be integrally formed with the distal portion 144 of the securement member 140 as a single unitary structure. Some suitable but non-limiting materials for the securement member 140, for example metallic materials, polymer materials, composite materials, etc., are described below.

In some embodiments, the proximal portion 142 of the securement member 140 may be configured to disengage from the distal portion 144 of the securement member 140. The proximal portion 142 of the securement member 140 may be fixedly attached to the proximal end of the release wire 120. The distal portion 144 of the securement member 140 may be fixedly attached to the proximal end 114 of the elongate shaft 110. In at least some embodiments, an outer surface of the distal portion 144 of the securement member 140 may be fixedly attached to an inner surface of the elongate shaft 110 (e.g., a surface defining the lumen 112). Alternatively, in some embodiments, an inner surface of the distal portion 144 of the securement member 140 may be fixedly attached to an outer surface of the elongate shaft 110. In some embodiments, the proximal portion 142 of the securement member 140 may be releasably secured to and/or configured to disengage from the distal portion 144 of the securement member 140 at a perforation 150 (see detail at FIGS. 8A and 8B) and/or a frangible link 160 (see detail at FIG. 9) formed in the wall 146 of the securement member 140.

In at least some embodiments, the securement member 140 may prevent axial translation of the release wire 120 relative to the elongate shaft 110 and/or the medical device 130 prior to disengagement of the proximal portion 142 of the securement member 140 from the distal portion 144 of the securement member 140. Disengaging the proximal portion 142 of the securement member 140 from the distal portion 144 of the securement member 140 may permit the release wire 120 to axially translate relative to the distal portion 144 of the securement member 140 and/or the elongate shaft 110. In other words, the wall 146 of the distal portion 144 of the securement member 140 may define a lumen, as seen in FIGS. 3 and 4 for example, wherein the release wire 120 is slidably disposed within the lumen of the distal portion 144 of the securement member 140. Upon disengagement of the proximal portion 142 of the securement member 140 from the distal portion 144 of the securement member 140, as seen in FIG. 4, axial translation of the proximal portion 142 relative to the distal portion 144 of the securement member 140 and/or the elongate shaft 110 may translate the release wire 120 relative to the elongate shaft 110 and/or the distal portion 144 of the securement member 140 to release the medical device 130 from the distal end 116 of the elongate shaft 110, as will be explained in more detail herein.

Figure 5:
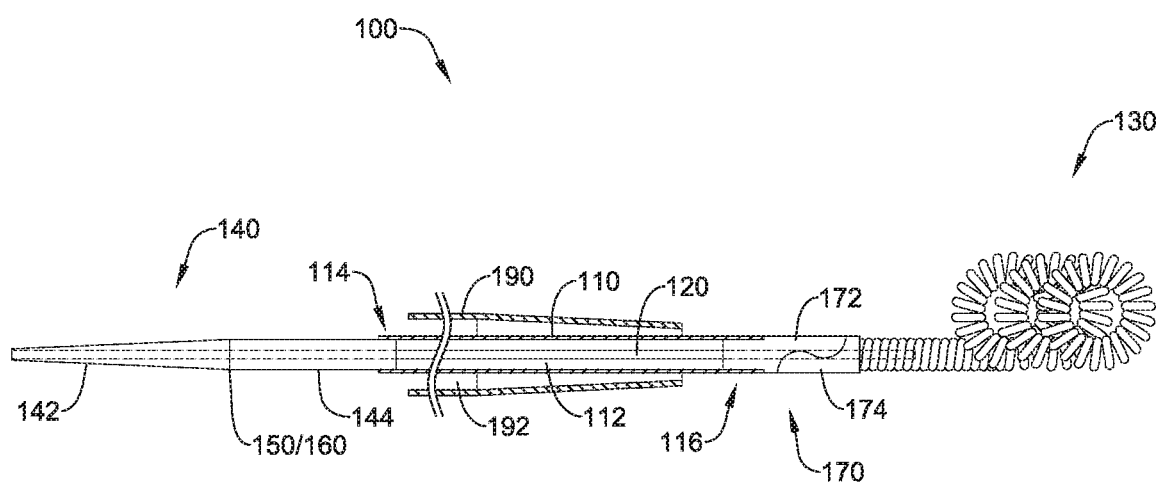
FIGS. 5-6 are partial cut-away views illustrating actuation of a portion of an example medical device system.
Figure 6:
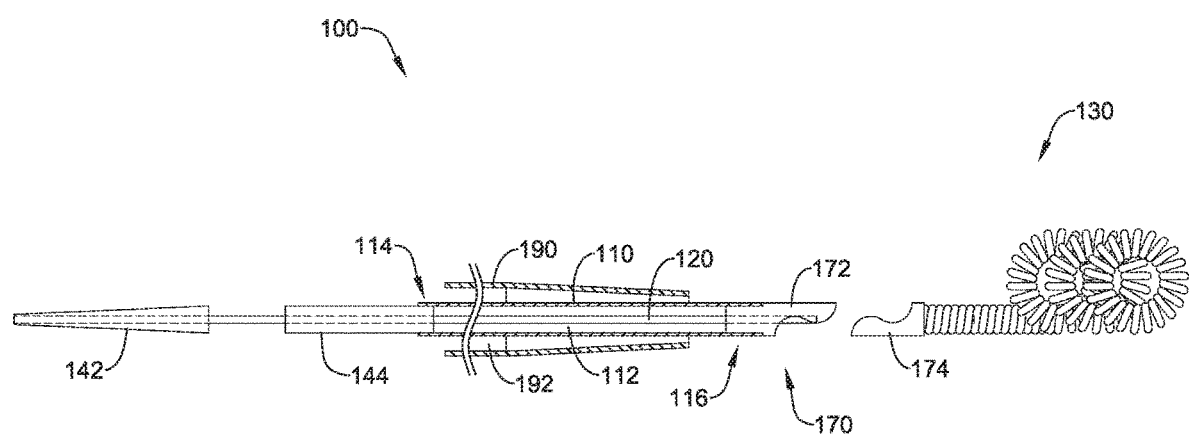

FIGS. 5 and 6 generally illustrate the medical device 130 being released from the elongate shaft 110, such as at a treatment site, for example. In use, the microcatheter 190 of the medical device system 100 may be inserted into a patient's anatomy and a distal end guided and/or advanced to a location adjacent a treatment site. The medical device 130 disposed at the distal end 116 of the elongate shaft 110 may be inserted into a proximal end of the lumen 192 disposed within the microcatheter 190 and advanced through the microcatheter 190 to the treatment site. In some embodiments, the medical device 130 may be disposed within the lumen 192 of the microcatheter 190 proximate to the distal end 116 of the elongate shaft 110. In some embodiments, the medical device 130 may be disposed within the lumen 192 of the microcatheter 190 proximate to the distal end 116 of the elongate shaft 110 prior to use and/or prior to inserting the microcatheter 190 into the patient's anatomy. Deployment and/or release of the medical device 130 may be performed selectively depending upon the type of medical device and/or the desired treatment process or method. When ready to deploy the medical device 130, the elongate shaft 110 may be advanced and/or translated distally relative to the microcatheter 190 until the medical device 130 is exposed and/or disposed distal of the microcatheter 190.

Figure 7:
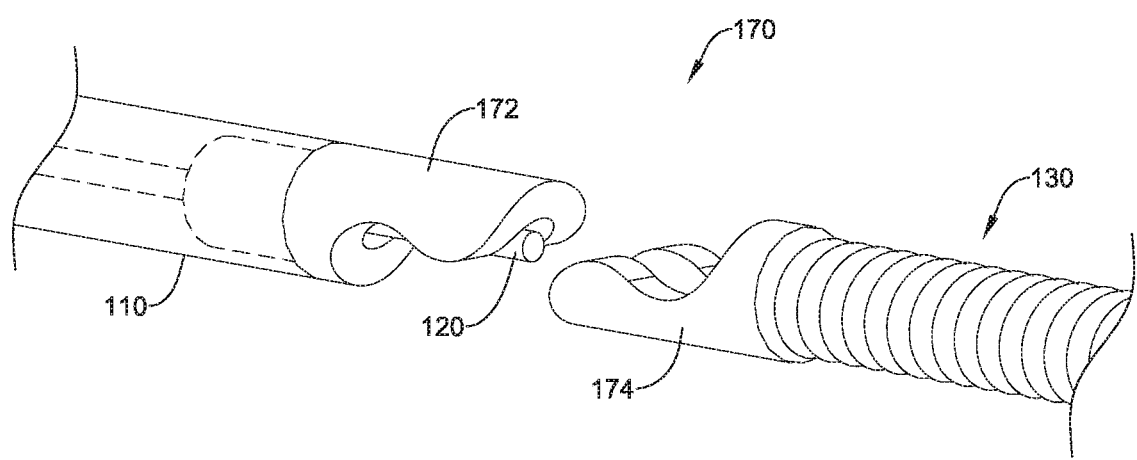
FIG. 7 illustrates an example release mechanism of an example medical device system.

A release mechanism 170 may releasably attach the medical device 130 to the distal end 116 of the elongate shaft 110. In some embodiments, the elongate shaft 110 may include a first portion 172 of the release mechanism 170 fixedly attached to the distal end 116 of the elongate shaft 110 and the medical device 130 may include a second portion 174 of the release mechanism 170 fixedly attached to a proximal end of the medical device 130. A distal end of the release wire 120 may slidably engage with the first portion 172 of the release mechanism 170 and the second portion 174 of the release mechanism 170, as seen in FIG. 5. The release wire 120 interlocks the first portion 172 of the release mechanism 170 with the second portion 174 of the release mechanism 170 when the proximal portion 142 of the securement member 140 is engaged with the distal portion 144 of the securement member 140. For example, when the proximal portion 142 of the securement member 140 is disengaged and/or separated from the distal portion 144 of the securement member 140, as seen in FIG. 6, the release wire 120 is translated in a proximal direction relative to the elongate shaft 110 to release the second portion 174 of the release mechanism 170 and/or the medical device 130 from the first portion 172 of the release mechanism 170 and/or the elongate shaft 110, as seen in more detail in FIG. 7. In at least some embodiments, the release wire 120 may be slidably disposed within the distal portion 144 of the securement member 140, the elongate shaft 110, the first portion 172 of the release mechanism 170, and the second portion 174 of the release mechanism 170. Some suitable but non-limiting materials for the release mechanism 170, for example metallic materials, polymer materials, composite materials, etc., are described below.

Referring back to FIGS. 5 and 6, the elongate shaft 110 may have sufficient length that the proximal end 114 of the elongate shaft 110 and/or the securement member 140 remain proximal of (e.g., extend proximally from) the microcatheter 190 when the medical device 130 is disposed distal of the microcatheter 190. In use, the elongate shaft 110 may have sufficient length to reach from the treatment site to a position outside of the patient where the medical device system 100 may be manipulated by an operator (e.g., clinician, physician, user, etc.). The operator of the medical device system 100 may then place a first hand on the distal portion 144 of the securement member 140 and a second hand on the proximal portion 142 of the securement member 140. The proximal portion 142 of the securement member 140 may be configured to disengage from the distal portion 144 of the securement member 140 at a location proximal of a proximal end of the microcatheter 190 when the medical device 130 is disposed distal of the microcatheter 130. In at least some embodiments, the proximal portion 142 of the securement member 140 may be disengaged from the distal portion 144 of the securement member 140 by bending, twisting, and/or pulling the proximal portion 142 of the securement member 140 relative to the distal portion 144 of the securement member 140. In some embodiments, disengaging the proximal portion 142 of the securement member 140 from the distal portion 144 of the securement member 140 may include moving the proximal portion 142 of the securement member 140 relative to the distal portion 144 of the securement member 140 to separate the proximal portion 142 of the securement member 140 from the distal portion 144 of the securement member 140. In some embodiments, disengaging the proximal portion 142 of the securement member 140 from the distal portion 144 of the securement member 140 may include using an external device (e.g., a torque device, an external handle, etc.) to move the proximal portion 142 of the securement member 140 relative to the distal portion 144 of the securement member 140.

Figure 8A:
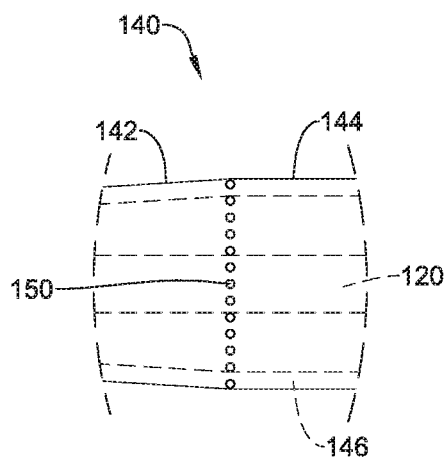
FIG. 8A illustrates a portion of an example securement member of an example medical device system.

FIG. 8A (detail "8" from FIG. 3) illustrates the securement member 140 including the perforation 150 formed in the wall 146 of the securement member 140. In at least some embodiments, the perforation 150 may include a series of apertures extending through the wall 146 of the securement member 140. In some embodiments, the perforation 150 may extend circumferentially about an entire circumference of the wall 146 of the securement member 140. In some embodiments, the perforation 150 may extend partially and/or intermittently about the entire circumference of the wall 146 of the securement member 140. While an exemplary series of apertures is illustrated in FIG. 8A as round holes, the skilled person will recognize that other suitable shapes (e.g., square, rectangular, ovoid, irregular, etc.) may also be used. For example, in some embodiments, the perforation 150 may include a series of rectangular notches having a major dimension oriented circumferentially, the series of rectangular notches extending through the wall 146 of the securement member 140. Additionally, while the perforation 150 and/or the exemplary series of apertures is illustrated in FIG. 8A as being generally oriented and/or positioned within a plane perpendicular to a longitudinal axis of the securement member 140, other orientations and/or positioning may be used. For example, in some embodiments, the perforation 150 and/or the series of apertures may be oriented and/or positioned within or along a plane at an oblique angle to the longitudinal axis of the securement member 140. Other, for example non-planar, configurations are also possible. The proximal portion 142 of the securement member 140 is disposed proximal of the perforation 150 and the distal portion 144 of the securement member 140 is disposed distal of the perforation 150. As mentioned above, the proximal portion 142 of the securement member 140 may be releasably secured to and/or configured to disengage from the distal portion 144 of the securement member 140 at the perforation 150 formed in the wall 146 of the securement member 140.

Figure 8B:
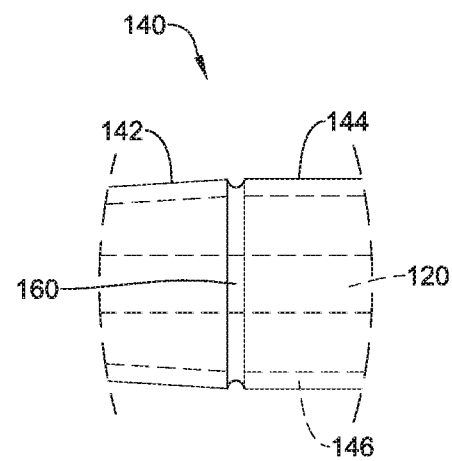
FIG. 8B illustrates a portion of an example securement member of an example medical device system.

FIG. 8B (detail "8" from FIG. 3) illustrates the securement member 140 including the frangible link 160 formed in the wall 146 of the securement member 140. In at least some embodiments, the frangible link 160 may include a thinned and/or weakened feature, or series of features, formed in the wall 146 of the securement member 140 that is more susceptible to fracture and/or separation than the remainder of the wall 146. In some embodiments, the frangible link 160 may extend circumferentially about an entire circumference of the wall 146 of the securement member 140. In some embodiments, the frangible link 160 may extend partially and/or intermittently about the entire circumference of the wall 146 of the securement member 140. The proximal portion 142 of the securement member 140 is disposed proximal of the frangible link 160 and the distal portion 144 of the securement member 140 is disposed distal of the frangible link 160. As mentioned above, the proximal portion 142 of the securement member 140 may be releasably secured to and/or configured to disengage from the distal portion 144 of the securement member 140 at the frangible link 160 formed in the wall 146 of the securement member 140.

In some embodiments, the securement member 140 may include the perforation 150 and the frangible link 160. For example, the perforation 150 may be formed within the frangible link 160. In some embodiments, a portion of the circumference of the securement member 140 may include the perforation 150 while a different portion of the circumference of the securement member 140 may include the frangible link 160. Other combinations and/or configuration are also contemplated.

Figure 9:
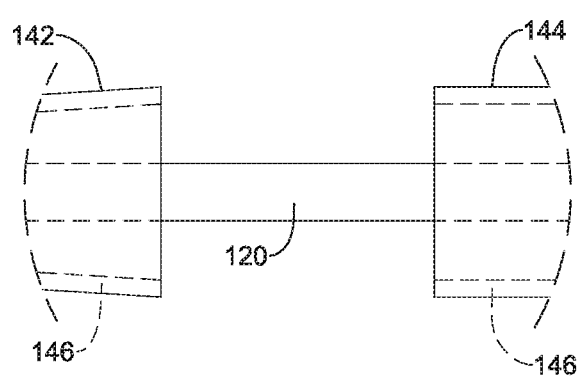
FIG. 9 illustrates a portion of an example securement member of an example medical device system.

FIG. 9 (detail "9" from FIG. 4) illustrates the securement member 140 after disengaging the proximal portion 142 of the securement member 140 from the distal portion 144 of the securement member 140 at the perforation 150 and/or the frangible link 160 and subsequent separation of the proximal portion 142 of the securement member 140 from the distal portion 144 of the securement member 140. Proximal translation of the proximal portion 142 of the securement member 140 relative to the distal portion 144 of the securement member 140 and/or the elongate shaft 110 results in the release wire 120 translating and/or sliding within and/or relative to the elongate shaft 110 and the distal portion 144 of the securement member 140.

Figure 10:
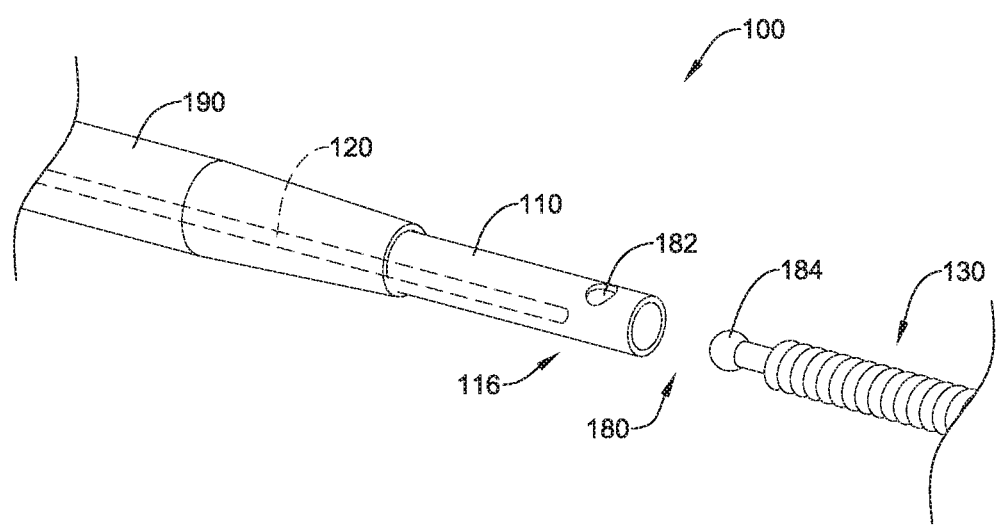
FIG. 10 illustrates an example release mechanism of an example medical device system.

In another example, FIG. 10 illustrates a release mechanism 180 that may releasably attach the medical device 130 to the distal end 116 of the elongate shaft 110. In some embodiments, the elongate shaft 110 may include a first portion 182 of the release mechanism 180 fixedly attached to the distal end 116 of the elongate shaft 110 and the medical device 130 may include a second portion 184 of the release mechanism 180 fixedly attached to a proximal end of the medical device 130. In the exemplary embodiment illustrated in FIG. 10, the first portion 182 of the release mechanism 180 may include an aperture or hole formed in a wall of the elongate shaft 110 proximate the distal end 116 of the elongate shaft 110, and the second portion 184 of the release mechanism 180 may include a ball or enlargement sized and configured to engage the aperture or hole of the first portion 182 of the release mechanism 180.

A distal end of the release wire 120 may slidably engage with the second portion 184 of the release mechanism 180 when the second portion 184 of the release mechanism 180 is engaged with and/or disposed within the first portion 182 of the release mechanism 180 and/or the distal end of the elongate shaft 110, thereby urging and/or pushing the second portion 184 of the release mechanism 180 into, and/or into engagement with, the first portion 182 of the release mechanism 180. The release wire 120 interlocks the first portion 182 of the release mechanism 180 with the second portion 184 of the release mechanism 180 when the proximal portion 142 of the securement member 140 is engaged with the distal portion 144 of the securement member 140. For example, when the proximal portion 142 of the securement member 140 is disengaged and/or separated from the distal portion 144 of the securement member 140, as seen in FIGS. 5 and 6, the release wire 120 is translated in a proximal direction relative to the elongate shaft 110 to release the second portion 184 of the release mechanism 180 and/or the medical device 130 from the first portion 182 of the release mechanism 180 and/or the elongate shaft 110, as seen in FIG. 10. In at least some embodiments, the release wire 120 may be slidably disposed within the distal portion 144 of the securement member 140, and the elongate shaft 110, and may slidably engage the second portion 184 of the release mechanism 180 proximate the first portion 182 of the release mechanism 180. Some suitable but non-limiting materials for the release mechanism 180, for example metallic materials, polymer materials, composite materials, etc., are described below.

The materials that can be used for the various components of the medical device system 100, the elongate shaft 110, the release wire 120, the medical device 130, the securement member 140, the release mechanism 170, and/or the release mechanism 180, etc. (and/or other systems disclosed herein) and the various elements thereof disclosed herein may include those commonly associated with medical devices. For simplicity purposes, the following discussion makes reference to the medical device system 100, the elongate shaft 110, the release wire 120, the medical device 130, the securement member 140, the release mechanism 170, and/or the release mechanism 180, etc. However, this is not intended to limit the devices and methods described herein, as the discussion may be applied to other elements, members, components, or devices disclosed herein, such as, but not limited to, the medical device system 100, the elongate shaft 110, the release wire 120, the medical device 130, the securement member 140, the release mechanism 170, and/or the release mechanism 180, etc. and/or elements or components thereof.

In some embodiments, the medical device system 100, the elongate shaft 110, the release wire 120, the medical device 130, the securement member 140, the release mechanism 170, and/or the release mechanism 180, etc., and/or components thereof (such as, but not limited to, the first portion 142, the second portion 144, the wall 146, the first portion 172, the second portion 174, the first portion 182, the second portion 184, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system 100, the elongate shaft 110, the release wire 120, the medical device 130, the securement member 140, the release mechanism 170, and/or the release mechanism 180, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system 100, the elongate shaft 110, the release wire 120, the medical device 130, the securement member 140, the release mechanism 170, and/or the release mechanism 180, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 100, the elongate shaft 110, the release wire 120, the medical device 130, the securement member 140, the release mechanism 170, and/or the release mechanism 180, etc. to achieve the same result.

In some embodiments, a degree of Magnetic Resonance Imaging (MRI) compatibility is imparted into the medical device system 100, the elongate shaft 110, the release wire 120, the medical device 130, the securement member 140, the release mechanism 170, and/or the release mechanism 180, etc. For example, the medical device system 100, the elongate shaft 110, the release wire 120, the medical device 130, the securement member 140, the release mechanism 170, and/or the release mechanism 180, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system 100, the elongate shaft 110, the release wire 120, the medical device 130, the securement member 140, the release mechanism 170, and/or the release mechanism 180, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system 100, the elongate shaft 110, the release wire 120, the medical device 130, the securement member 140, the release mechanism 170, and/or the release mechanism 180, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device 130 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device system, comprising:
   an elongate shaft having a lumen extending from a proximal end of the elongate shaft to a distal end of the elongate shaft;
   a release wire disposed within the lumen of the elongate shaft, wherein the release wire is configured to releasably attach a medical device to the distal end of the elongate shaft; and
   a securement member fixedly attached to the proximal end of the elongate shaft and to a proximal end of the release wire;
   wherein a proximal portion of the securement member is configured to disengage from a distal portion of the securement member;
   wherein the proximal portion of the securement member is disengaged from the distal portion of the securement member by bending or pulling the proximal portion of the securement member relative to the distal portion of the securement member,
   wherein the securement member is sized to be received within the proximal end of the elongate shaft and is free from an external handle that moves the proximal portion of the securement member relative to the distal portion of the securement member.

2. The medical device system of claim 1, wherein the proximal portion of the securement member is fixedly attached to the proximal end of the release wire and the distal portion of the securement member is fixedly attached to the proximal end of the elongate shaft.

3. The medical device system of claim 2, wherein an outer surface of the distal portion of the securement member is fixedly attached to an inner surface of the elongate shaft.

4. The medical device system of claim 1, wherein disengaging the proximal portion of the securement member from the distal portion of the securement member permits the release wire to axially translate relative to the elongate shaft.

5. The medical device system of claim 4, wherein axial translation of the proximal portion of the securement member relative to the distal portion of the securement member axially translates the release wire relative to the elongate shaft.

6. The medical device system of claim 1, wherein the proximal portion of the securement member is integrally formed with the distal portion of the securement member.

7. The medical device system of claim 1, wherein the securement member includes a perforation formed in a wall of the securement member.

8. The medical device system of claim 7, wherein the proximal portion of the securement member is disposed proximal of the perforation and the distal portion of the securement member is disposed distal of the perforation.

9. The medical device system of claim 1, wherein the securement member includes a frangible link formed in a wall of the securement member.

10. The medical device system of claim 9, wherein the proximal portion of the securement member is disposed proximal of the frangible link and the distal portion of the securement member is disposed distal of the frangible link.

11. A medical device system, comprising:
    an elongate shaft having a lumen extending from a proximal end of the elongate shaft to a distal end of the elongate shaft;
    a medical device disposed proximate the distal end of the elongate shaft;

a release wire disposed within the lumen of the elongate shaft, wherein the release wire releasably secures the medical device to the distal end of the elongate shaft;

a securement member fixedly attached to the proximal end of the elongate shaft and to a proximal end of the release wire; and a microcatheter configured to deliver the medical device to a treatment site, the elongate shaft and the medical device being slidably disposed within a lumen of the microcatheter;

wherein a proximal portion of the securement member is configured to disengage from a distal portion of the securement member;

wherein the proximal portion of the securement member is disengaged from the distal portion of the securement member by bending or pulling the proximal portion of the securement member relative to the distal portion of the securement member, wherein the securement member is sized to be received within the proximal end of the elongate shaft and is free from an external handle that moves the proximal portion of the securement member relative to the distal portion of the securement member.

12. The medical device system of claim 11, wherein the proximal portion of the securement member is configured to disengage from the distal portion of the securement member at a location proximal of the microcatheter when the medical device is disposed distal of the microcatheter.

13. The medical device system of claim 11, wherein the proximal portion of the securement member is configured to disengage from the distal portion of the securement member at a perforation formed in a wall of the securement member.

14. The medical device system of claim 11, wherein the elongate shaft includes a first portion of a release mechanism attached to the distal end of the elongate shaft and the medical device includes a second portion of the release mechanism attached to a proximal end of the medical device;

wherein the release wire interlocks the first portion of the release mechanism with the second portion of the release mechanism when the proximal portion of the securement member is engaged with the distal portion of the securement member.

* * * * *